United States Patent [19]

Jaeggi

[11] Patent Number: 5,110,807
[45] Date of Patent: May 5, 1992

[54] ARALIPHATYLAMINOALKANEDIPHOSPHONIC ACIDS

[75] Inventor: Knut A. Jaeggi, Basel, Switzerland

[73] Assignee: Ciba-Geigy Corporation, Ardsley, N.J.

[21] Appl. No.: 500,441

[22] Filed: Mar. 28, 1990

Related U.S. Application Data

[63] Continuation-in-part of Ser. No. 278,394, Dec. 1, 1988, abandoned.

[51] Int. Cl.$^5$ .................. A61K 31/66; C07F 9/38
[52] U.S. Cl. .......................... 514/89; 514/94; 514/95; 514/107; 514/108; 549/6; 562/13; 548/112; 548/119
[58] Field of Search .............. 562/13; 546/22; 548/112, 119; 549/6; 514/89, 94, 95, 107, 108

[56] References Cited

U.S. PATENT DOCUMENTS

| | | | |
|---|---|---|---|
| 3,683,080 | 8/1972 | Francis | 424/204 |
| 4,054,598 | 10/1977 | Blum et al. | 260/502.5 |
| 4,624,947 | 11/1986 | Blum et al. | 514/108 |
| 4,687,767 | 8/1987 | Basles et al. | 514/89 |
| 4,719,203 | 1/1988 | Bosies et al. | 514/108 |
| 4,761,406 | 8/1988 | Flora et al. | 514/86 |
| 4,777,163 | 10/1988 | Bosies et al. | 514/80 |
| 4,871,720 | 10/1989 | Jaeggi | 514/79 |

FOREIGN PATENT DOCUMENTS

| | | |
|---|---|---|
| 186405 | 7/1986 | European Pat. Off. |
| 224751 | 6/1987 | European Pat. Off. |
| 252504 | 1/1988 | European Pat. Off. |

OTHER PUBLICATIONS

No. 874860 Abstract.

Primary Examiner—Mukund J. Shah
Assistant Examiner—Y. N. Gupta
Attorney, Agent, or Firm—Irving M. Fishman; Karen G. Kaiser

[57] ABSTRACT

Araliphatylaminoalkanediphosphonic acids of formula

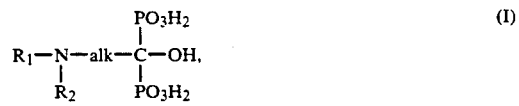

wherein $R_1$ is an aromatically substituted aliphatic radical, $R_2$ is hydrogen or a monovalent aliphatic radical and alk is a divalent aliphatic radical, and their salts, exhibit a pronounced regulatory action on the calcium metabolism and can be used as medicaments for the treatment of diseases that are attributable to calcium metabolism disorders. They are prepared, for example, by reacting a compound of formula

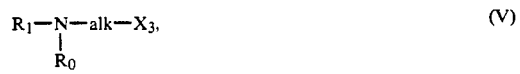

wherein $X_3$ is a carboxy and $R_0$ is a radical $R_2$, with phosphorous acid and phosphorous trichloride and hydrolysing the primary product.

21 Claims, No Drawings

ARALIPHATYLAMINOALKANEDIPHOSPHONIC ACIDS

This a continuation-in-part of my co-pending patent application Ser. No. 278,394, filed Dec. 1, 1988, now abandoned.

The invention relates to araliphatylaminoalkanediphosphonic acids of formula

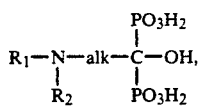

wherein $R_1$ is an aromatically substituted aliphatic radical, $R_2$ is hydrogen or a monovalent aliphatic radical and alk is a divalent aliphatic radical, and their salts, to processes for the preparation of the compounds of the invention, to pharmaceutical compositions containing them and to their use as active ingredients in medicaments.

Aromatically substituted aliphatic radicals $R_1$ are, for example, lower alkyl or lower alkenyl radicals that are substituted by at least one aromatic or heteroaromatic radical. Aromatic and heteroaromatic substituents are, for example, 5- or 6-membered monocyclic aryl radicals, or bicyclic aryl radicals composed of 5- or 6-membered rings, or 5- or 6-membered monocyclic heteroaryl radicals, or bicyclic heteroaryl radicals composed of 5- or 6-membered rings, which heteroaryl radicals contain as hetero atom(s) 1 or 2 N-atoms, 1 O-atom or S-atom, 1 N-atom and 1 O-atom, or 1 N-atom and 1 S-atom, such as phenyl or, secondly, naphthyl or pyrrolyl, thienyl, furyl, pyridyl, imidazoyl, pyrimidinyl or quinolinyl, especially phenyl, thienyl, pyridyl or imidazolyl, each of which aryl and heteroaryl radicals is unsubstituted or, especially, is mono- or poly-substituted, preferably mono- or, secondly, di-substituted, by lower alkyl, lower alkoxy, lower alkylthio and/or by halogen. The radical $R_1$ may be substituted by one or more than one such substituent $R_3$, for example by one substituent $R_3$ or by two identical or different substituents $R_3$. These are preferably bonded by way of a carbon atom but may also be bonded by way of an additional nitrogen atom which may be present. If $R_1$ has more than one such substituent, preferably two of these are bonded to the same carbon atom of the aliphatic radical.

Preferred radicals $R_1$ are those of formula

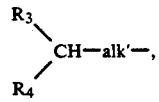

wherein $R_3$ is an aromatic radical $R_A$, $R_4$ is hydrogen or an aromatic radical $R_B$ and alk' is lower alkylene, $R_A$ and $R_B$ each having one of the meanings given for R and the sum of the carbon atoms of alk' preferably not exceeding 6.

Monovalent aliphatic radicals are, for example, lower alkyl or lower alkenyl radicals, and divalent aliphatic radicals are especially lower alkylene radicals.

Hereinafter there are to be understood by lower radicals and compounds, for example, those radicals and compounds having up to and including 7, especially up to and including 4, carbon atoms. The general terms also have, for example, the following meanings:

Lower alkyl is, for example, $C_1$–$C_4$alkyl, such as methyl, ethyl, propyl, isopropyl or butyl, and also isobutyl, secondary butyl or tertiary butyl, but may also be a $C_5$–$C_7$alkyl group, such as a pentyl, hexyl or heptyl group.

Lower alkoxy is, for example, $C_1$–$C_4$alkoxy, such as methoxy, ethoxy, propoxy, isopropoxy or butoxy, and also isobutoxy, secondary butoxy or tertiary butoxy.

Lower alkylthio is, for example, $C_1$–$C_4$alkylthio, such as methylthio, ethylthio, propylthio or butylthio, and also isobutylthio, secondary butylthio or tertiary butylthio.

Halogen is, for example, halogen having an atomic number of up to and including 35, such as chlorine or fluorine, and also bromine.

Lower alkenyl is, for example, $C_2$–$C_4$alkenyl, such as vinyl, allyl or buten-2-yl, but may also be a $C_5$–$C_7$alkenyl group, such as pentenyl, hexenyl or heptenyl group.

Lower alkylene alk is, for example, $C_2$–$C_4$alkylene, especially straight-chained $C_2$–$C_4$-alkylene, such as $\alpha,\omega$-$C_2$–$C_4$-alkylene, for example ethylene, 1,3-propylene or, secondly, 1,4-butylene.

Lower alkylene alk' is, for example, $C_2$–$C_6$alkylene, especially straight-chained $C_2$–$C_6$alkylene, such as $\alpha,\omega$-$C_2$–$C_6$alkylene, for example ethylene, 1,3-propylene, 1,4-butylene, 1,5-pentylene or 1,6-hexylene, but may also be 1,2-propylene, 1,2- or 1,3-butylene or 1,4-pentylene.

Salts of compounds of formula I are especially internal salts thereof and salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, copper salts, aluminium salts or zinc salts, or ammonium salts with ammonia or organic amines or quaternary ammonium bases, such as optionally C-hydroxylated aliphatic amines, especially mono-, di- or tri-lower alkylamines, for example methyl-, ethyl-, dimethyl- or diethyl-amine, mono- di- or tri-(hydroxy-lower alkyl)-amines, such as ethanol-, diethanol- or triethanol-amine, tris(hydroxymethyl)amino-methane or 2-hydroxy-tert.-butylamine, or N-(hydroxy-lower alkyl)-N,N-di-lower alkylamines or N-(polyhydroxy-lower alkyl)N-lower alkylamines, such as 2-(dimethylamino)-ethanol or D-glucamine, or quaternary aliphatic ammonium hydroxides, for example tetrabutylammonium hydroxide. These salts include both complete salts and partial salts, i.e. salts with 1, 2, 3 or 4, preferably 2, equivalents of base per mole of the acid of formula I.

The compounds of formula I and their salts have valuable pharmacological properties. In particular, they exhibit a pronounced regulatory action on the calcium metabolism of warm-blooded animals. In particular, in rats, they effect a marked inhibition of bone resorption, which can be demomstrated both in the test procedure according to Acta Endocrinol. 78,613-24 (1975) by reference to the PTH-induced increase in the serum calcium level after subcutaneous administration in doses of from approximately 0.01 to approximately 1.0 mg/kg, and in the TPTX (thyroparathyroidectomised) rat model by reference to the experimental hypercalcaemia, induced by vitamin $D_3$, after the administration of doses of approximately from 0.001 to 1.0 mg s.c.. The tumour hypercalcaemia induced by Walker-256- tumours is likewise inhibited after peroral administration of from approximately 1.0 to approximately 100 mg/kg. Further, in adjuvant arthritis in rats in the test procedure according to Newbould, Brit. J. Pharmacology 21, 127 (1963) and according to Kaibara et al., J. Exp. Med. 159, 1388-96 (1984), they exhibit a marked inhibition of the progression of chronic arthritic processes in doses of approximately from 0.01 to 1.0 mg/kg s.c.. They are therefore eminently suitable as active ingredients in medicaments for the treatment of diseases that may be associated with calcium metabolism disorders, for example inflammatory processes in joints and degenerative processes in the articular cartilage, of osteoporosis, periodontitis, hyperparathyroidism and of calcium deposits in blood vessels or on prosthetic implants. A favourable effect is produced both in dieases in which an anomalous deposition of sparingly soluble calcium salts is to be observed, such as diseases from among the forms of arthritis, for example Brechterew's disease, neuritis, bursitis, periodontitis and tendinitis, fibrodysplasia, osteoarthrosis and arteriosclerosis, and in diseases in which an anomalous degeneration of hard body tissue is the principal symptom, such as hereditary hypophosphatasia, degenerative processes in the articular cartilage, osteoporoses of various origins, Paget's disease and osteodystrophia fibrosa, and also in tumour-induced osteolytic processes.

The invention relates, for example, to compounds of formula I wherein $R_1$, $R_2$ and alk have the meanings given at the beginning, with the proviso that in compounds of formula I wherein $R_1$ is monosubstituted by phenyl, $R_2$ is hydrogen or, if $R_1$ contains 2 or 3 carbon atoms in the aliphatic moiety, is an aliphatic radical containing at most 3 carbon atoms, and their salts.

The invention relates especially to compounds of formula I wherein $R_1$ is a lower alkyl or lower alkenyl radical that is mono- or di-substituted by a 6-membered monocyclic aryl radical or by a bicylic aryl radical composed of 5- or 6-membered rings or by a 5- or 6-membered monocyclic heteroaryl radical or by a bicyclic heteroaryl radical composed of 5- or 6-membered rings, which heteroaryl radicals contain as hetero atom(s) 1 or 2 N-atom(s), 1 O-atom or 1 S-atom, 1 N-atom and 1 O-atom, and 1 S-atom, and which aryl and heteroaryl radicals are unsubstituted or substituted by lower alkyl, lower alkoxy, lower alkylthio and/or by halogen, $R_2$ is hydrogen, lower alkyl or lower alkenyl, and alk is lower alkylene, for example those wherein $R_2$ is hydrogen or $C_1$-$C_3$alkyl and $R_1$ in the aliphatic moiety contains 2 or 3 carbon atoms if $R_1$ is substituted by unsubstituted phenyl, and their salts, especially their pharmaceutically acceptable salts.

The invention relates especially, for example, to compounds of formula I wherein $R_1$ is a lower alkyl radical that is mono- or di- substituted by a 6-membered monocyclic aryl radical or by a bicyclic aryl radical composed of 5- and/or 6-membered rings, which aryl radicals are unsubstituted or substituted by lower alkyl, lower alkoxy, lower alkylthio and/or by halogen, or is a lower alkyl radical that is mono-substituted by a 5- or 6-membered monocyclic heteroaryl radical that contains as hetero atom(s) 1 O-atom or S-atom or 1 or 2 N-atoms, $R_2$ is hydrogen or a lower alkyl radical, with the proviso that $R_2$ is hydrogen if $R_1$ is an unsubstituted benzyl- or phenyl-$C_3$-$C_7$alkyl radical, or that $R_2$ is hydrogen or lower alkyl containing 1 to 2 carbon atoms if $R_1$ is a phenethyl radical, and alk is lower alkylene, and their salts.

The invention relates especially to compounds of formula I wherein $R_1$ is a radical of formula (Ia) wherein $R_3$ is an aromatic radical $R_A$, $R_4$ is hydrogen or an aromatic radical $R_B$ and alk' is lower alkylene, $R_A$ and $R_B$ each being a 5- or 6-membered monocyclic aryl radical or a bicyclic aryl radical composed of 5- or 6-membered rings or a 5- or 6-membered monocyclic heteroaryl radical or a bicyclic heteroaryl radical composed of 5- or 6-membered rings, which heteroaryl radicals contain as hetero atom(s) 1 or 2 N-atom(s), 1 O-atom or S-atom, 1 N-atom and 1 O-atom or 1 N-atom and 1 S-atom, and which aryl and heteroaryl radicals are unsubstituted or substituted by lower alkyl, lower alkoxy, lower alkylthio and/or by halogen, $R_2$ is hydrogen, lower alkyl or lower alkenyl, and alk is lower alkylene, for example those wherein alk' is $C_2$-$C_3$lower alkylene and $R_2$ is hydrogen or $C_1$-$C_3$alkyl if $R_3$ is unsubstituted phenyl and $R_4$ is hydrogen, and their salts, especially their pharmaceutically acceptable salts.

The invention relates more especially, on the one hand, to compounds of formula I wherein $R_1$ is a radical of formula (Ia) wherein $R_3$ is a phenyl, thienyl, pyridyl, imidazolyl or naphthyl radical that is unsubstituted or mono- or di-substituted by $C_1$-$C_4$alkyl, such as methyl, $C_1$-$C_4$alkoxy, such as methoxy, $C_1$-$C_4$alkylthio, such as methylthio, and/or by halogen having an atomic number of up to and including 35, such as fluorine or chlorine, $R_4$ is hydrogen or, if $R_3$ is a phenyl radical that is unsubstituted or mono- or di-substituted by $C_1$-$C_4$alkyl, such as methyl, $C_1$-$C_4$alkoxy, such as methoxy, $C_1$-$C_4$alkylthio, such as methylthio, and/or by halogen having an atomic number of up to and including 35, such as fluorine or chlorine, $R_4$ is likewise a phenyl radical that is unsubstituted or mono- or di-substituted by $C_1$-$C_4$alkyl, such as methyl, $C_1$-$C_4$alkoxy, such as methoxy, $C_1$-$C_4$alkylthio, such as methylthio, and/or by halogen having an atomic number of up to and including 35, such as fluorine or chlorine, alk' is $C_1$-$C_5$alkylene, such as ethylene, 1,3-propylene or 1,4-butylene, $R_2$ is hydrogen, and alk is straight-chained $C_2$-$C_4$alkylene, such as ethylene or 1,3-propylene, and their salts, especially their pharmaceutically acceptable salts.

The invention relates more especially, on the other hand, to compounds of formula I wherein $R_1$ is a radical of formula (Ia) wherein $R_3$ is a phenyl, naphthyl, thienyl, pyridyl or imidazolyl radical that is unsubstituted or mono- or di-substituted by $C_1$-$C_4$alkyl, such as methyl, $C_1$-$C_4$alkoxy, such as methoxy, $C_1$-$C_4$alkylthio, such as methylthio, and/or by halogen having an atomic number of up to and including 35, such as fluorine or chlorine, $R_4$ is hydrogen or, if $R_3$ is a phenyl radical that is unsubstituted or mono-or di-substituted by $C_1$-$C_4$alkyl, such as methyl, $C_1$-$C_4$alkoxy, such as methoxy, $C_1$-$C_4$alkylthio, such as methylthio, and/or by halogen having an atomic number of up to and including 35, such as fluorine or chlorine, $R_4$ is likewise a phenyl radical that is unsubstituted or mono- or di-substituted by $C_1$-$C_4$alkyl, such as methyl, $C_1$-$C_4$alkoxy, such as methoxy, $C_1$-$C_4$alkylthio, such as methylthio, and/or by halogen having an atomic number of up to and including 35, such as fluorine or chlorine, alk' is $C_1$-$C_5$alkylene, such as 1,3-propylene, 1,4-butylene or 1,5-pentylene, $R_2$ is $C_1$-$C_4$alkyl, such as methyl, or $C_2$-$C_4$alkenyl, such as allyl, and alk is straight-chained $C_2$-$C_4$alkylene, such as ethylene or 1,3-propylene, with the proviso that alk' is methylene and $R_2$ is hydrogen or $C_1$-$C_2$alkyl if $R_3$ is unsubstituted phenyl and $R_4$ is hydrogen, and their salts, especially their pharmaceutically acceptable salts.

The invention relates preferably to compounds of formula I wherein $R_1$ is a radical of formula (Ia) wherein $R_3$ is phenyl that is unsubstituted or, secondly, mono- or di-substituted by $C_1$–$C_4$alkyl, such as methyl, $C_1$–$C_4$-alkoxy, such as methoxy, or by halogen having an atomic number of up to and including 35, such as chlorine or fluorine, $R_4$ is hydrogen, alk' is straight-chained, terminally bonded $C_2$–$C_4$alkylene, such as ethylene or 1,3-propylene, $R_2$ is hydrogen or $C_1$–$C_4$alkyl, such as methyl, and alk is $C_2$–$C_3$alkylene, such as ethylene, for example those wherein alk' is $C_1$–$C_2$-alkylene and $R_2$ is hydrogen or $C_1$–$C_3$alkyl if $R_3$ is unsubstituted phenyl, and their salts, especially their pharmaceutically acceptable salts.

The invention relates most preferably to compounds of formula I wherein $R_1$ is mono- or di-phenyl-$C_2$–$C_6$alkyl that is unsubstituted or mono- or di-substituted in the phenyl moiety by $C_1$–$C_4$alkyl, such as methyl, $C_1$–$C_4$-alkoxy, such as methoxy, and/or by halogen having an atomic number of up to and including 35, such as chlorine, or is imidazolyl-, thienyl- or pyridyl-$C_2$–$C_6$alkyl, $R_2$ is hydrogen or $C_1$–$C_4$-alkyl, such as methyl, and alk is $C_2$–$C_3$-alkylene, such as ethylene, with the proviso that $R_2$ is hydrogen if $R_1$ is unsubstituted phenyl-$C_3$–$C_6$alkyl, or $R_2$ is hydrogen or $C_1$–$C_2$alkyl if $R_1$ is an unsubstituted phenethyl radical, and their salts, especially their pharmaceutically acceptable salts.

The invention relates most especially to compounds of formula I wherein $R_1$ is a radical of formula (Ia) wherein $R_3$ is phenyl that is unsubstituted or, secondly, mono- or di-substituted by $C_1$–$C_4$alkyl, such as methyl, $C_1$–$C_4$-alkoxy, such as methoxy, and/or by halogen having an atomic number of up to and including 35, such as chlorine or fluorine, $R_4$ is hydrogen, alk' is straight-chained, terminally bonded $C_2$–$C_4$alkylene, such as ethylene or 1,3-propylene, $R_2$ is hydrogen, and alk is $C_2$–$C_3$alkylene, such as ethylene, and their salts, especially their pharmaceutically acceptable salts.

The invention relates specifically to the compounds of formula I mentioned in the Examples and their salts, especially their internal salts and pharmaceutically acceptable salts with bases.

The invention also relates to a process for the preparation of compounds of formula I and their salts, which process is based on methods that are known per se. This process comprises a) in a compound of formula

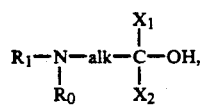

(II)

wherein $R_0$ is a radical $R_2$ or an amino-protecting group and $X_1$ is a functionally modified phosphono group and $X_2$ is a free or functionally modified phosphono group, converting functionally modified phosphono $X_1$ and, where appropriate, $X_2$ into a free phosphono group, or b) reacting compounds of formulae $R_1$—$Y_1$     (III)

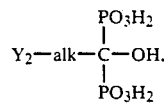

(IV)

wherein one of the radicals $Y_1$ and $Y_2$ is a reactive esterified hydroxy group and the other is a group of formula —N($R_0$)—H wherein $R_0$ is a radical $R_2$ or an amino-protecting group, or salts thereof, with each other, or c) reacting a compound of formula

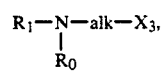

(V)

wherein $R_0$ is a radical $R_2$ or an amino-protecting group and $X_3$ is carboxy, carbamoyl or cyano, especially carboxy or cyano, with phosphorous acid and phosphorus trichloride, hydrolysing the primary product and, in an intermediate of formula

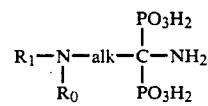

(VI)

obtained starting from compounds of formula V wherein $X_3$ is cyano or carbamoyl, or in a salt thereof, replacing the amino group by hydroxy by treatment with nitrous acid, and in each case removing the amino-protecting group if present and, if desired, converting a resulting compound into a different compound of formula I and/or converting a resulting free compound into a salt or a resulting salt in the free compound or into a different salt.

Suitable amino-protecting groups $R_0$ are, for example, α-aryl-lower alkyl, such as benzyl or p-methoxybenzyl, α,α,α-triaryl-lower alkyl, such as trityl, or tri-lower alkylsilyl, such as trimethysilyl. α-Aryl- and α,α,α-tri-aryl-lower alkyl can readily be removed by hydrogenolysis, and tri-lower alkylsilyl and α,α,α-tri-aryl-lower alkyl can readily be removed by hydrolysis. The removal of α-aryl- and α,α,α-tricosyl-lower alkyl $R_0$ using hydrogenolysis is effected especially by reaction with hydrogen in the presence of a hydrogenation catalyst, such as a nickel or noble metal catalyst, for example palladium-on-carbon, preferably in a lower alkanol under normal pressure and temperature conditions, for example at approximately from 20° C. to 30° C. and from approximately 0.95 bar to approximately 1.3 bar.

Functionally modified phosphono groups that are to be converted into free phosphono in accordance with process variant a) are, for example, in the form of an ester, especially in the form of a diester of formula —P(=O)(OR)$_2$ (IIa) wherein OR is etherified hydroxy, for example lower alkoxy, lower alkanoyloxy-lower alkoxy, such as $C_2$–$C_7$alkanoyloxy-$C_1$–$C_4$-alkoxy, for example acetoxymethoxy or pivaloyloxymethoxy, or is a phenoxy, α-phenyl-lower alkoxy or silyloxy group each unsubstituted or substituted by lower alkyl, lower alkoxy, halogen, trifluoromethyl and/or by hydroxy, such as tri-lower alkylsilyloxy.

The conversion of functionally modified phosphono groups into free phosphono groups is effected in customary manner, such as by hydrolysis, for example in the presence of a mineral acid, such as hydrochloric or sulfuric acid, at from approximately 80° C. to approximately 110° C., for example at boiling temperature, or by reaction with a tri-lower alkylhalosilane, for example trimethylchlorosilane or, especially, trimethyliodosilane or trimethylbromosilane, preferably in methylene chloride, in a temperature range of from approximately 0° to approximately 40° C., and by subsequent treatment with water. α-Phenyl-lower alkyl esters can furthermore be converted into compounds of formula I by hydrogenolysis, for example reaction with hydrogen in the presence of a hydrogenation catalyst, such as a nickel or noble metal catalyst, for example palladium-on-carbon, preferably in a lower alkanol under normal pressure and temperature conditions.

The starting materials of formula II can be prepared, for example, by reacting a compound of formula

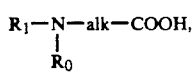 (IIb)

or preferably the anhydride or acid chloride thereof, with a corresponding phosphorous acid triester of formula $P(OR)_3$ (IIc), for example at from 0° C. to approximately 60° C., to give a compound of formula

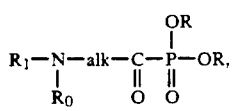 (IId)

and further reacting the latter with a phosphorous acid diester of formula $H—P(=O)(OR)_2$ (IIe) or $P(OH)(OR)_2$ (IIf) in the presence of a di-lower alkylamine, for example diethylamine, or in the presence of an alkali metal lower alkanolate, for example sodium methanolate, to give the corresponding compound of formula

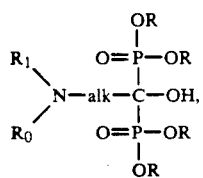 (IIg)

Starting materials of formula IIb can, if they are not known, be prepared, for example, by reacting a corresponding compound of formula

 (IIh), wherein $R_0$ is a group $R_2$ or an amino-protecting group, with a compound of formula

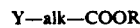 (IIi), wherein Y is halogen, such as bromine, or, for the preparation of compounds IIb wherein alk is 1,2-lower alkylene, for example ethylene, with a compound of formula

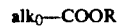 (IIj), wherein $alk_0$ is lower alk-1-enyl, hydrolysing the ester obtained in each case to the acid and anhydridising or chlorinating the latter, for example using phosphorus pentachloride, and, if desired, removing the amino-protecting group if present.

Reactive esters (III) and (IV) that are to be used in accordance with process variant b) contain as the reactive esterified hydroxy group, for example, a halogen atom, such as a chlorine, bromine or iodine atom, or a sulfonyloxy group, such as an alkanesulfonyloxy group or an unsubstituted or substituted benzenesulfonyloxy group, for example methanesulfonyloxy or p-toluenesulfonyloxy.

The reaction with the reactive esters mentioned is effected, for example, in the presence of a base, such as an alkali metal hydroxide or an alkaline earth metal hydroxide, for example sodium hydroxide, or a quaternary ammonium hydroxide, for example tetrabutylammonium hydroxide, advantageously in the presence of a solvent or diluent, for example a lower alkanol, a di-lower alkyl ketone or a cycloaliphatic ether, for example isopropanol, methyl ethyl ketone, dioxane or tetrahydrofuran.

The starting materials of formula IV can be prepared, for example, by reacting a compound of formula

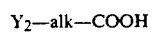 (IVa)

in customary manner, for example in chlorobenzene, with phosphorous acid and phosphorus trichloride or with phosphoric acid and an excess of phosphorus tribromide, and subsequently working up by hydrolysis.

The reaction of compounds of formula V with phosphorous acid and phosphorus trichloride in accordance with process variant c) is effected in customary manner, the phosphorous acid component preferably being formed in situ by reaction of excess phosphorus trichloride with water-containing phosphoric acid, for example with commercially customary approximately 75% to approximately 95%, preferably approximately 85%, phosphoric acid. The reaction is advantageously carried out while heating, for example at from approximately 70° to approximately 120° C., in a suitable solvent, such as tetrachloroethane, trichloroethane, chlorobenzene, chlorotoluene or paraffin oil, and with working up being effected by hydrolysis.

The treatment of intermediates of formula VI with nitrous acid is effected in customary manner with the latter being freed in aqueous solution from one of its salts, for example sodium nitrite, by acid treatment, for example by the action of hydrochloric acid, during which a corresponding, unstable diazonium salt, for example diazonium chloride, is formed as intermediate, which diazonium salt, with the introduction of the ?-hydroxy group, splits off nitrogen.

The starting materials of formula V can, if they are not known, be prepared, for example, by reacting a corresponding compound of formula

 (IIh), wherein $R_0$ is a group $R_2$ or an amino-protecting group, with a compound of formula

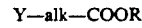 (IIi), wherein Y is halogen, such as bromine, or, for the preparation of compounds of formula V wherein alk is 1,2-lower alkylene, for example ethylene, with a compound of formula $$alk_0—X_3 \quad (III),$$

wherein $alk_0$ is a lower alk-1-enyl radical, and in each case removing the amino-protecting group if present and, if desired, in each case hydrolysing the resulting primary product to the acid.

Compounds of formula I obtained by the process of the invention or by another method that is known per se can be converted into other compounds of formula I in a manner known per se.

For example, in a resulting compound of formula I wherein $R_2$ is hydrogen, by reaction with a lower alkanal under reducing conditions, for example with formaldehyde and formic acid, or, secondly, with a reactive ester of a lower alkanol or lower alkenol in customary manner, preferably in the presence of a basic condensing agent, such as an alkali metal lower alkanolate, hydrogen can be replaced by a lower alkyl or lower alkenyl radical $R_2$, respectively.

Furthermore, non-aromatic double bonds present in $R_1$ and/or $R_2$ can be reduced to single bonds in customary manner by hydrogenolysis, for example reaction with hydrogen in the presence of a hydrogenation catalyst, such as a nickel or noble metal catalyst, for example palladium-on-carbon, preferably in a lower alkanol under normal pressure and temperature conditions.

The aromatic substituent(s) of $R_1$ can also be substituted. For example, halogen can be introduced by reaction with a customary nuclear halogenating agent, for example with chlorine or bromine in the presence of a Lewis acid, such as iron(III) chloride.

Depending on the starting materials and procedures chosen, the novel compounds may be obtained in the form of one of the possible isomers or as a mixture thereof, for example depending on the number of asymmetric carbon atoms, they may be obtained in the form of pure optical isomers, such as antipodes, or in the form of isomeric mixtures, such as racemates, diastereoisomeric mixtures or mixtures of racemates.

Resulting diastereoisomeric mixtures and mixtures of racemates can be separated on the basis of the physico-chemical differences between the components into the pure isomers, diastereoisomers or racemates in known manner, for example by chromatography and/or fractional crystallisation.

Resulting racemates can furthermore be resolved into the optical antipodes by known methods, for example by recrystallisation from an optically active solvent, with the aid of microorganisms, or by reaction of an acid end product with an optically active base that forms salts with the racemic acid and by separation of the salts obtained in that manner, for example on the basis of their differing solubilities, into the diastereoisomers from which the antipodes can be freed by the action of suitable agents. Advantageously, the more active of the two antipodes is isolated.

Resulting free compounds of formula I, including their internal salts of formula I, can be converted into salts with bases by partial or complete neutralisation with one of the bases mentioned at the beginning. Acid addition salts also can be converted in an analogous manner into the corresponding free compounds or internal salts thereof.

Conversely, resulting free compounds of formula I can be converted into acid addition salts by treatment with a protonic acid.

Resulting salts can be converted in a manner known per se into other salts having a lower proportion of cations (partial salts) or into the free compounds, for example by treatment with an acid reagent, such as a mineral acid. Resulting free compounds can be converted by treatment with a base, for example alkali hydroxide solution, into salts and/or resulting salts having a lower proportion of cations (partial salts) can be converted in the same manner into salts having a higher proportion of cations, for example complete salts.

The compounds, including their salts, may also be obtained in the form of their hydrates or may include the solvent used for crystallisation.

Owing to the close relationship between the novel compounds in free form and in the form of their salts, throughout this specification there is to be understood by the free compounds or their salts, where appropriate and expedient, also the corresponding salts or free compounds, respectively.

The invention relates also to those embodiments of the process in which a compound obtainable as an intermediate at any stage of the process is used as starting material and the remaining steps are carried out, or a starting material is used in the form of a salt and/or racemate or antipode or, especially, is formed under the reaction conditions.

The starting materials used in the present invention are preferably those which result in the compounds described at the beginning as being especially valuable. The invention relates also to novel starting materials and to processes for the preparation thereof.

The pharmaceutical preparations according to the invention, which contain compounds of formula I or pharmaceutically acceptable salts thereof, are for enteral, such as oral or rectal, and parenteral administration and contain the pharmacologically active ingredient on its own or together with a pharmaceutically acceptable carrier.

The novel pharmaceutical preparations contain, for example, from approximately 10% to approximately 80%, preferably from approximately 20% to approximately 60%, active ingredient. Pharmaceutical preparations according to the invention for enteral and parenteral administration are, for example, those in dosage unit form, such as dragées, tablets, capsules or suppositories, and also ampoules. These are prepared in a manner known per se, for example by means of conventional mixing, granulating, confectioning, dissolving or lyophilising processes. For example, pharmaceutical preparations for oral administration can be obtained by combining the active ingredient with solid carriers, if desired granulating a resulting mixture and processing the mixture or granulate, if desired or necessary after the addition of suitable adjuncts, into tablets or dragée cores.

Suitable carriers are especially fillers, such as sugars, for example lactose, saccharose, mannitol or sorbitol, and cellulose preparations, and also binders, such as starch pastes using, for example, corn, wheat, rice or potato starch, gelatine, tragacanth, methylcellulose and/or polyvinylpyrrolidone, and/or, if desired, disintegrators, such as the above-mentioned starches, also carboxymethyl starch, crosslinked polyvinyl-pyrrolidone, agar, alginic acid or a salt thereof, such as sodium alginate. Adjuncts are especially flow-regulating and lubricating agents, for example silica, talc, stearic acid and/or polyethylene glycol. Dragée cores are provided with suitable coatings which may be resistant to gastric juices, there being used, inter alia, concentrated sugar solutions which may contain gum arabic, talc, polyvinylpyrrolidone, polyethylene glycol and/or titanium dioxide, or lacquer solutions in a suitable organic solvents or solvent mixtures, or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules consisting of gelatine, and also soft sealed capsules consisting of gelatine and a plasticiser, such as glycerol or sorbitol. The dry-filled capsules may contain the active ingredient in the form of a granulate, for example in admixture with fillers, such as lactose, binders, such as starches, and/or glidants, such as talc, and, if desired, stabilisers. In soft capsules, the active ingredient is preferably dissolved or suspended in suitable liquids, such as fatty oils, paraffin oil or liquid polyethylene glycols, to which stabilisers may also be added.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatine rectal capsules that contain a combination of the active ingredient with a base material; suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, or suspensions of the active ingredient, such as corresponding oily injection suspensions, in which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran and, if desired, also stabilisers.

The present invention relates also to the use of compounds of formula I and their salts, preferably for the treatment of diseases that are attributable to calcium metabolism disorders, for example of the rheumatic type, and especially of osteoporoses.

Dosages under 0.01 mg/kg body weight have only a negligible effect on pathological calcification or the degeneration of hard tissue. At dosages above 100 mg/kg body weight, toxic side-effects may occur in long-term use. The compounds of formula I and their salts can be administered both orally and, in the form of a hypertonic solution, subcutaneously, intramuscularly or intravenously. The preferred daily doses are in the range of approximately from 0.1 to 5 mg/kg in the case of oral administration, in the range of approximately from 0.1 to 1 mg/kg in the case of subcutaneous and intramuscular administration, and in the range of approximately from 0.01 to 2 mg/kg, for example approximately from 0.013 to 0.67 mg/kg, in the case of intravenous administration.

The dosage of the compounds used is, however, variable and depends on the particular conditions, such as the nature and severity of the disease, the duration of treatment and on the particular compound. Single doses contain, for example, from 0.01 to 10 mg, dosage unit forms for parenteral, such as intravenous, administration contain, for example, from 0.01 to 0.1 mg, preferably from 0.02 to 0.08 mg, and oral dosage unit forms contain, for example, from 0.2 to 2.5 mg, preferably from 0.3 to 1.5 mg, per kg of body weight. The preferred single dosage for oral administration is from 10 to 100 mg and for intravenous administration from 0.5 to 5 mg, and can be administered up to 4 times per day. The higher dosages in the case of oral administration are necessary owing to the limited resorption. In the case of long-term treatments, the initially higher dosage can normally be changed to lower dosages while still maintaining the desired effect.

The following Examples illustrate the invention described above; they are not intended, however, to limit the scope thereof in any way. Temperatures are given in degrees Celsius.

EXAMPLE 1

(0.1 mol) of 3-[N-(3-phenylpropyl)-N-methylamino]-propionic acid hydrochloride is heated at 100° under reflux with 13.4 ml of 85% phosphoric acid and 50 ml of chlorobenzene while stirring. Then, at 100°, 27 ml of phosphorus trichloride are added dropwise, gas evolution taking place. A thick mass separates from the reaction mixture over the course of 30 minutes. The mixture is heated at 100° for a further 3 hours and the supernatant chlorobenzene is then removed by decanting. The viscous mass which remains is refluxed with 100 ml of 9N hydrochloric acid for 3 hours while stirring. The mixture is filtered while hot, with the addition of carbon, and the filtrate is diluted with acetone, whereupon 3-[N-(3-phenylpropyl)-N-methyl-amino]-1-hydroxy-propane-1,1-diphosphonic acid separates out in crystalline form; m.p. 219° (decomposition).

The 3-[N-(3-phenylpropyl)-N-methyl-amino]-propionic acid hydrochloride used as starting material can be prepared as follows:

(0.15 mol) of N-(3-phenylpropyl)-N-methyl-amine are introduced into 50 ml of diethyl ether, and 15.1 g of ethyl acrylate are gradually added thereto while stirring. With a slight increase in temperature, a clear solution forms. After standing overnight at room temperature, the ether is removed by distillation. The oil which remains is crude 3-[N-(3-phenylpropyl)-N-methyl-amino]-propionic acid ethyl ester.

The resulting ester is refluxed with 600 ml of 4N hydrochloric acid for 24 hours. The mixture is then completely concentrated by evaporation under reduced pressure and the crystalline residue is triturated with acetone. After the crystals have been filtered with suction, washed and dried, 3-[N-(3-phenylpropyl)-N-methyl-amino]-propionic acid hydrochloride is obtained.

EXAMPLE 2

In a manner analogous to that described in Example 1, 3-(3-phenylpropylamino)-1-hydroxy-propane-1,1-diphosphonic acid, m.p. 219° (decomp.), 3-(3-phenyl-prop-2-ylamino)-1-hydroxy-propane-1,1-diphosphonic acid, m.p. 208°-210° (decomp.), 3-[N-(3-phenylpropyl)-N-ethyl-amino]-1-hydroxy-propane-1,1-diphosphonic acid, m.p. 195°-197° (decomp.), 3-(4-phenylbutylamino)-1-hydroxy-propane-1,1-diphosphonic acid, m.p. 191°-193° (decomp.) and 3-[3-(pyrid-3-yl)propylamino]-1-hydroxy-propane-1,1-diphosphonic acid can be obtained starting from or via 3-(3-phenylpropylamino)-propionic acid hydrochloride (m.p. 219°, decomp.), 3-(3-phenylprop-2-ylamino)-propionic acid hydrochloride (m.p. 126°–127°), 3-[N-(3-phenylpropyl)-N-ethyl-amino]-propionic acid hydrochloride, oil, 3-(4-phenylbutylamino)-propionic acid hydrochloride, m.p. 135°–137° and 3-[3-(pyrid-3-yl)propylamino]-propionic acid hydrochloride, respectively.

EXAMPLE 3

9.3 g (26.3 mmol) of 3-(3-phenylpropylamino)-1-hydroxypropane-1,1-diphosphonic acid are refluxed for 36 hours with 6.1 ml of formic acid and 4.2 ml of a 38% formaldehyde solution in water. The reaction solution is concentrated by evaporation under reduced pressure and the residue is diluted with acetone, yielding 3-[N-(3-phenylpropyl)-N-methyl-amino]-1-hydroxy-propane-1,1-diphosphonic acid in the form of colourless crystals of m.p. 219° (decomp.).

EXAMPLE 4

In a manner analogous to that described in Example 1, 3-[4,4-di(p-fluorophenyl)butylamino]-1-hydroxy-propane-1,1-diphosphonic acid, m.p. 220°–222° (decomp.) is obtained starting from 3-[4,4-di(p-fluorophenyl)-butylamino]-propionic acid ethyl ester via 3-[4,4-di(p-fluorophenyl)butylamino]-propionic acid hydrochloride, m.p. 165°–166°.

The starting material can be prepared, for example, in the following manner:

26.1 g (0.1 mol) of 4,4-di(p-fluorophenyl)butylamine and 18.1 g of 3-bromopropionic acid ethyl ester are refluxed with 21.0 g of potassium carbonate in 200 ml of 2-butanone for 24 hours while stirring. The reaction mixture is filtered and the filtrate is concentrated by evaporation under reduced pressure, yielding crude 3-[4,4-di(p-fluorophenyl)-butylamino]-propionic acid ethyl ester in the form of an oil.

In an analogous manner, 4-[N-(2-phenethyl)-N-methyl-amino]-1-hydroxybutane-1,1-diphosphonic acid is obtained starting from N-(2-phenethyl)-N-methyl-amine and 4-bromobutyric acid ethyl ester via 4-[N-(2-phenethyl)-N-methyl-amino]-butyric acid ethyl ester and 4-[N-(2-phenethyl)-N-methylamino]butyric acid hydrochloride.

EXAMPLE 5

In a manner analogous to that described in Example 1, 3-{N-[3-imidazol-4-yl)propyl]-N-methyl-amino}-1-hydroxy-propane-1,1-d iphosphonic acid is obtained starting from N-[3-(imidazol-4-yl)propyl]-N-methyl-amine via 3-{N-[3-(imidazol-4-yl)propyl]-N-methyl-amino}-propionic acid ethyl ester and 3-{N-[3-(imidazol-4-yl)propyl]N-methyl-amino}-propionic acid hydrochloride.

The starting material can be prepared, for example, in the following manner:

16.8 g (0.12 mol) of 3-[imidazol-4(5)-yl]propionic acid are refluxed with 13.1 ml of thionyl chloride for 2 hours. After removing excess thionyl chloride by distillation, 3-[imidazol-4(5)-yl]propionic acid chloride hydrochloride remains as a semi-solid mass (yield 100%).

23.4 g (0.12 mol) of 3-[imidazol-4(5)-yl]propionic acid chloride hydrochloride are dissolved in 80 ml of dimethylformamide and the solution is cooled to −10°. Methylamine gas is passed into the solution for 2 hours until there has been a weight increase of 15 g. After standing overnight at room temperature, the reaction mixture is concentrated to dryness by evaporation under reduced pressure. The residue is chromatographed on 220 g of silica gel with the eluant chloroform/methanol/conc. ammonia (80:20:1). The fractions containing the product yield, from tetrahydrofuran, colourless crystals of 3-[imidazol-4(5)-yl]propionic acid (N-methyl)amide, m.p. 168°–170°. 10.9 g (0.0718 mol) of 3-[imidazol-4(5)-yl]propionic acid (N-methyl)amide are added in portions, while stirring, to a suspension of 2.8 g of lithium aluminium hydride in 200 ml of tetrahydrofuran and the reaction mixture is then refluxed for 30 hours. The reaction mixture is then cooled to 0°, and 3 ml of water, 2.2 ml of 10N sodium hydroxide solution and 8.2 ml of water are added dropwise in succession. The inorganic precipitate is filtered off and the filtrate is concentrated by evaporation in vacuo. The oil which remains is crude N-[imidazol-4(5)-yl-propyl]-N-methylamine.

EXAMPLE 6

In a manner analogous to that described in Example 1,

3-[4-(4-methoxyphenyl)butylamino]-1-hydroxy-propane-1,1-diphosphonic acid, m.p. 160°–164° (decomp.);

3-[3-(4-methoxyphenyl)propyl-N-methyl-amino]-1-hydroxy-propane-1,1-diphosphonic acid, m.p. 154°–156° (decomp.);

3-[3-(4-chlorophenyl)propyl-N-methyl-amino]-1-hydroxy-propane-1,1-diphosphonic acid, m.p. 162°–166° (decomp.);

3-[3-(3-methylphenyl)propyl-N-methyl-amino]-1-hydroxy-propane-1,1-diphosphonic acid, m.p. 193°–195° (decomp.);

3-[3-(imidazol-4(5)-yl)propyl-N-methyl-amino]-1-hydroxy-propane-1,1-diphosphonic acid, m.p. 130°–136° (decomp.);

3-[3-(pyrid-2-yl)propyl-N-methyl-amino]-1-hydroxy-propane-1,1-diphosphonic acid, m.p. 142°–147° (decomp.);

3-[N-(2-phenethyl)-N-methyl-amino]-1-hydroxy-propane-1,1-diphosphonic acid, m.p. 187°–188° (decomp.); and 3-[N-(2-phenethyl)amino]-1-hydroxy-propane-1,1-diphosphonic acid, m.p. 205°–206° (decomp.) can be prepared starting from or via 3-[4-(4-methoxyphenyl)butylamino]propionic acid hydrochloride, m.p. 150°–152°;

3-[3-(4-methoxyphenyl)propyl-N-methyl-amino]propionic acid hydrochloride, m.p. 108°–110°;

3-[3-(4-chlorophenyl)propyl-N-methyl-amino]propionic acid hydrochloride, m.p. 128°–130°;

3-[3-(3-methylphenyl)propyl-N-methyl-amino]propionic acid hydrochloride, m.p. 97°–98°;

3-[3-(imidazol-4(5)-yl)propyl-N-methyl-amino]propionic acid dihydrochloride;

3-[3-(pyrid-2-yl)propyl-N-methyl-amino]propionic acid dihydrochloride, m.p. 157-160 (decomp.);

3-[N-(2-phenethyl)-N-methyl-amino]propionic acid hydrochloride, m.p. 144°–145° (decomp.); and 3-[N-(2-phenethyl)amino]propionic acid hydrochloride, m.p. 150°–152° (decomp.) respectively.

EXAMPLE 7

1,83 g of 3-(4-phenylbutylamino)-1-hydroxy-propane-1,1-diphosphonic acid are dissolved in 10 ml of 1N sodium hydroxide solution. The resulting solution is concentrated by evaporation under reduced pressure. The product is precipitated by addition of methanol allowed to crystallised and isolated by suction-filtration.

Disodium-3-(4-phenylbutylamino)-1-hydroxy-propane-1,1-diphosphonate of m.p. 313°–316° (decomp.) is thus obtained.

In an analogous manner, disodium-3-[N-(3-phenylpropyl)-N-methyl-amino]-1-hydroxypropane-1,1-diphosphonate of m.p. 321°–325° is obtained.

EXAMPLE 8

A Mixture of 22.2 g (0.1 mol) of 3-{N-[3-(pyrid-4-yl)propyl]-N-methylamino}-propionic acid hydrochloride, 13.4 ml of phosphoric acid (85%) and 50 ml of chlorobenzene are heated, with stirring to 100°. Then, 27 ml of phosphorus trichloride are added after which gas evolution sets in. Within 30 minutes a viscous mass separates. Heating is continued for additional 3 hours. The chlorobenzene layer is decanted off. 100 ml of 9-n hydrochloric acid are added and the reaction mixture is refluxed for 3 hours. The reactions solution is filtered hot with addition of charcoal, and the filtrate is diluted with acetone, upon which crystalline 3-{N-[3-(pyrid-4-yl)propyl]-N-methyl-amino}-1-hydroxy-propane-1,1-diphosphonic acid separates which is then collected and dried.

The starting material can be obtained as follows:

15.1 g of ethyl acrylate are added portionwise to a solution of 22.5 g (0,15 Mol) of N-[3-(pyrid-4-yl)propyl]-N-methyl-amine in 50 ml of diethyl ether. The clear solution formed is allowed to stand overnight. The solvent is evaporated off. Ethyl 3-{N-[3-(pyrid-4-yl)propyl]-N-methyl-amino}-propionate is thus obtained as an oil.

The ethyl 3-{N-[3-(pyrid-4-yl)propyl]-N-methyl-amino}-propionate obtained is refluxed for 24 hours with 600 ml of 4-n hydrochloric acid. The reaction mixture is evaporated to complete dryness, and the crystalline residue formed is separated, washed with water and dried yielding 3-{N-[3-(pyrid-4-yl)propyl]-N-methyl-amino}-propionic acid hydrochloride.

EXAMPLE 9

In an analogous manner as described in Example 8
3-{N-[2-(pyrid-2-yl)ethyl]-N-methyl-amino}-1-hydroxy-propane-1,1-diphosphonic acid and its hydrochloride (m.p. 155°–163°);
3-{N-[2-(pyrid-4yl)ethyl]-N-methyl-amino}-1-hydroxy-propane-1,1-diphosphonic acid and its hydrochloride (m.p. 133°–136°);
3-{N-[3-(pyrid-3-yl)propyl]-N-methyl-amino}-1-hydroxy-propane-1,1-diphosphonic acid and
3-{N-[4-(pyrid-2-yl)butyl]-N-methyl-amino}-1-hydroxy-propane-1,1-diphosphonic acid and its hydrochloride (m.p. 140°–142°)
can be obtained starting from
3-{N-[2-(pyrid-2-yl)ethyl]-N-methyl-amino}-propionic acid hydrochloride;
3-{N-[2-(pyrid-4-yl)ethyl]-N-methyl-amino}-propionic acid hydrochloride;
3-{N-[3-(pyrid-3-yl)propyl]-N-methyl-amino}-propionic acid hydrochloride and
3-{N-[4-(pyrid-2-yl)butyl]-N-methyl-amino}-propionic acid hydrochloride.

EXAMPLE 10

3,68 g (0,01 mol) of 3-{N-[4-(pyrid-2-yl)butyl]-N-methyl-amino}-1-hydroxy-propane-1,1-diphosphonic acid are dissolved in 10 ml of a n- aqueous sodium hydroxide solution. The clear solution obtained is concentrated under reduced pressure. Methanol is added and the crystalline precipitate formed is filtered off and dried yielding monosodium 3-{4-(pyrid-2-yl)butyl]-N-methyl-amino}-1-hydroxy-propane-1,1-diphosphonate of m.p. >300°(decomp.).

EXAMPLE 11

Tablets, each containing 75 mg of active ingredient, for example 3-[N-(3-phenylproyl)-N-methyl-amino]-1-hydroxy-propane-1,1-diphosphonic acid or a salt thereof, for example the disodium salt, can be prepared in the following manner:

| Constituents (for 1000 tablets) | |
|---|---|
| active ingredient | 75.0 g |
| lactose | 268.5 g |
| corn starch | 22.5 g |
| polyethylene glycol 6000 | 5.0 g |
| talcum | 15.0 g |
| magnesium stearate | 4.0 g |
| demineralised water | q.s. |

Preparation

The solid ingredients are first forced through a sieve of 0.6 mm mesh width. Then, the active ingredient, lactose, talcum, magnesium stearate and half of the starch are homogeneously mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed into tablets of approximately 10 mm diameter which are concave on both sides and have a breaking notch on the upper side.

EXAMPLE 12

Tablets, each containing 10 mg of active ingredient, for example 3-[N-(3-phenylpropyl)-N-methyl-amino]-1-hydroxy-propane-1,1-diphosphonic acid or a salt thereof, for example the disodium salt, can be prepared in the following manner:

| Constituents (for 1000 tablets) | |
|---|---|
| active ingredient | 10.0 g |
| lactose | 328.5 g |
| corn starch | 17.5 g |
| polyethylene glycol 6000 | 5.0 g |
| talcum | 25.0 g |
| magnesium stearate | 4.0 g |
| demineralised water | q.s. |

Preparation

The solid ingredients are first forced through a sieve of 0.6 mm mesh width. Then, the active ingredient, lactose, talcum, magnesium stearate and half of the starch are homogeneously mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed into tablets of approximately 10 mm diameter which are concave

17 on both sides and have a breaking notch on the upper side.

EXAMPLE 13

Gelatine dry-filled capsules, each containing 100 mg of active ingredient, for example 3-[N-(3-phenyl-propyl)-N-methyl-amino]-1-hydroxypropane-1,1-diphosphonic acid or a salt thereof, for example the disodium salt, can be prepared in the following manner:

| Constituents (for 1000 capsules) | |
| --- | --- |
| active ingredient | 350.0 g |
| microcrystalline cellulose | 30.0 g |
| sodium lauryl sulfate | 2.0 g |
| magnesium stearate | 8.0 g |

The sodium lauryl sulfate is added to the active ingredient (lyophilised) through a sieve of mesh width 0.2 mm and the two components are intimately mixed for 10 minutes. The microcrystalline cellulose is then added through a sieve of mesh width 0.9 mm and the mixture is again intimately mixed for 10 minutes. Finally, the magnesium stearate is added through a sieve of mesh width 0.8 mm and, after mixing for a further 3 minutes, the mixture is introduced into size 0 (elongated) gelatine dry-filled capsules in portions of 390 mg.

EXAMPLE 14

A 0.2% injection or infusion solution can be prepared, for example, in the following manner:

| | |
| --- | --- |
| active ingredient, for example 3-[N-(3-phenylpropyl)-N-methyl-amino]-1-hydroxy-propane-1,1-diphosphonic acid or a salt thereof, for example the disodium salt | 5.0 g |
| sodium chloride | 22.5 g |
| phosphate buffer pH = 7.4 | 300.0 g |
| demineralised water | ad 2500.0 ml |

The active ingredient is dissolved in 1000 ml of water and filtered through a microfilter. The buffer solution is added and then water is added to give a volume of 2500 ml. For the preparation of dosage unit forms, portions of 1.0 or 2.5 ml are introduced into glass ampoules (containing 2.0 or 5.0 mg of active ingredient, respectively).

What is claimed is:

1. An aromatically substituted alkylaminoalkanediphosphonic acid of the formula

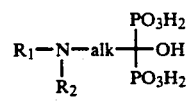
(I)

wherein $R_1$ is a lower alkyl or lower alkenyl radical that is mono- or di-substituted by at least one ring selected from phenyl and naphthyl, which ring is unsubstituted or substituted by at least one substituent selected from lower alkyl, lower alkoxy, lower alkylthio, and halogen; $R_2$ is hydrogen, lower alkyl, or lower alkenyl; and alk is lower alkylene; or a salt thereof.

2. The compound of claim 1 wherein $R_1$ is lower alkyl that is mono- or di-substituted by at least one ring selected from phenyl and naphthyl, which ring is unsubstituted or substituted by at least one substituent selected from lower alkyl, lower alkoxy, lower alkylthio, and halogen; $R_2$ is hydrogen or a lower alkyl; with the proviso that $R_2$ is hydrogen if $R_1$ is an unsubstituted benzyl- or phenyl-$C_{3-7}$alkyl, or that $R_2$ is hydrogen or lower alkyl containing 1 or 2 carbon atoms if $R_1$ is phenethyl, and alk is lower alkylene, or a salt thereof.

3. The compound of claim 1 wherein $R_1$ is a radical of the formula

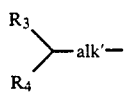
(Ia)

wherein $R_3$ is an aromatic radical $R_A$, $R_4$ is hydrogen or an aromatic radical $R_B$ and alk' is lower alkylene, $R_A$ and $R_B$ each being phenyl or naphthyl which is unsubstituted or substituted by at least one substituent selected from lower alkyl, lower alkoxy, lower alkylthio, and halogen; $R_2$ is hydrogen, lower alkyl, or lower alkenyl; and alk is lower alkylene; or a salt thereof.

4. A compound according to claim 1, with the proviso that in compounds of formula I wherein $R_1$ is mono-substituted by phenyl, $R_2$ is hydrogen or, if $R_1$ contains 2 or 3 carbon atoms in the aliphatic moiety, is an aliphatic radical containing at most 3 carbon atoms, or a salt thereof.

5. A compound according to claim 4 of formula I wherein $R_1$ is a radical of formula

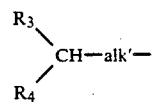
(Ia)

wherein $R_3$ is a phenyl radical that is unsubstituted or mono-substituted by $C_1$-$C_4$alkyl, $C_1$-$C_4$alkoxy, $C_1$-$C_4$alkylthio and/or by halogen having an atomic number of up to and including 35 or denotes naphthyl radical that is unsubstituted, $R_4$ is hydrogen or alk' is $C_1$-$C_5$alkylene, $R_2$ is hydrogen, and alk is straight-chained $C_2$-$C_4$alkylene, or a salt thereof.

6. A compound according to claim 1 of formula I wherein $R_1$ is a radical of formula

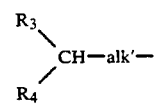
(Ia)

wherein $R_3$ is a naphthyl radical that is unsubstituted, $R_4$ is hydrogen, alk' is straight-chained $C_1$-$C_5$alkylene, $R_2$ is $C_1$-$C_4$alkyl or $C_2$-$C_4$alkenyl, and alk is straight-chained $C_2$-$C_4$alkylene, or a salt thereof.

7. A compound according to claim 1 of formula I wherein $R_1$ is a radical of formula

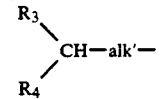
(Ia)

wherein $R_3$ is phenyl that is unsubstituted or mono-substituted by $C_1$-$C_4$alkyl $C_1$-$C_4$alkoxy and/or halogen having an atomic number of up to and including 35, $R_4$ is hydrogen, alk' is straight-chained, terminally bonded $C_2$-alkylene, $R_2$ is hydrogen or $C_1$-$C_3$alkyl, and alk is $C_2$-$C_3$alkylene, or a salt thereof.

8. A compound according to claim 1, wherein $R_1$ is lower alkyl radical that is mono- or disubstituted by a phenyl or a naphthyl that is unsubstituted or substituted by lower alkyl, lower alkoxy, lower alkylthio or halogen, $R_2$ is hydrogen or lower alkyl with the proviso that $R_2$ is hydrogen if $R_1$ is an unsubstituted benzyl or phenyl-$C_3$-$C_7$alkyl radical or $R_2$ is hydrogen or lower alkyl containing 1 or 2 carbon atoms if $R_1$ is a phenethyl radical, or a salts thereof.

9. A compound according to claim 1 of formula I wherein $R_1$ is mono- or di-phenyl-$C_2$-$C_6$alkyl that is unsubstituted or mono-substituted in the phenyl moiety by $C_1$-$C_4$alkyl, $C_1$-$C_4$alkoxy and/or by halogen having an atomic number of up to and including 35, $R_2$ is hydrogen or $C_1$-$C_4$alkyl, and alk is $C_2$-$C_3$alkylene, with the proviso that $R_2$ is hydrogen if $R_1$ is unsubstituted phenyl-$C_3$-$C_6$alkyl, or $R_2$ is hydrogen or $C_1$-$C_2$alkyl if $R_1$ is an unsubstituted phenethyl radical, or a salt thereof.

10. A compound according to claim 1 being 3-[N-(3-phenylpropyl)-N-methylamino]-1-hydroxy-propane-1,1-diphosphonic acid or a salt thereof.

11. A compound according to claim 1 being 3-(3-(Phenylpropylamino)-1-hydroxy-propane-1,1-diphosphonic acid or a salt thereof.

12. A compound according to claim 1 being 3-[N-(3-phenylpropyl)-N-ethylamino]-1-hydroxy-propane-1,1-diphosphonic acid or a salt thereof.

13. A compound according to claim 1 being 3-(4-Phenylbutylamino)-1-hydroxy-propane-1,1-diphosphonic acid or a salt thereof.

14. A compound according to claim 1 being 3-[4-(4-Methoxyphenyl)butylamino]-1-hydroxy-propane-1,1-diphosphonic acid or a salt thereof.

15. A compound according to claim 1 being 3-[3-(4-Methoxyphenyl)propyl-N-methylamino]-1-hydroxy-propane-1,1-diphosphonic acid or a salt thereof.

16. A compound according to claim 1 being 3-[3-(4-Chlorophenyl)propyl-N-methylamino]-1-hydroxy-propane-1,1-diphosphonic acid or a salt thereof.

17. A compound according to claim 1 being 3-[3-(3-Methylphenyl)propyl-N-methylamino]-1-hydroxy-propane-1,1-diphosphonic acid or a salt thereof.

18. A compound according to claim 1 being 3-[N-(2-phenethyl)amino]-1-hydroxy-propane-1,1-diphosphonic acid or a salt thereof.

19. A compound according to claim 1 being 3-[N-(2-phenethylethyl)-N-methyl-amino]-1-hydroxy-propane-1,1-diphosphonic acid or a salt thereof.

20. A pharmaceutical composition containing a compound according to claim 1 together with customary pharmaceutical carriers.

21. A method of treating diseases that are associated with calcium metabolism disorders, which comprises administering a compound according to claim 1.

* * * * *

UNITED STATES PATENT AND TRADEMARK OFFICE
CERTIFICATE OF CORRECTION

PATENT NO. : 5,110,807
DATED : May 5, 1992
INVENTOR(S) : Knut A. Jaeggi

It is certified that error appears in the above-indentified patent and that said Letters Patent is hereby corrected as shown below:

Column 18, line 8, claim 2, change "benzyl-" to --benzyl--.
Column 18, line 8, claim 5, change "hydrogen or alk' " to -- hydrogen, alk'--.
Column 18, line 5, claim 7, change "$C_1$-$C_4$alkyl $C_1$ - $C_4$alkoxy" to --$C_1$-$C_4$alkoxy--.
Column 19, line 9, claim 8, change "salts" to --salt--.
Column 20, line 2, claim 19, change "phenethylethyl" to --phenethyl--.

Signed and Sealed this

Twenty-eighth Day of September, 1993

Attest:

BRUCE LEHMAN

*Attesting Officer*     *Commissioner of Patents and Trademarks*